United States Patent [19]

Rolfe

[11] 4,289,975
[45] Sep. 15, 1981

[54] DISSIPATING ELECTRICAL CHARGE

[75] Inventor: Norman F. Rolfe, Carlisle, Mass.

[73] Assignee: Waters Associates, Inc., Milford, Mass.

[21] Appl. No.: 59,292

[22] Filed: Jul. 20, 1979

[51] Int. Cl.³ .................... H03K 17/04; H03K 17/12
[52] U.S. Cl. .................................. 307/246; 307/603; 307/353; 328/151
[58] Field of Search ................ 328/151; 307/246, 294, 307/352, 353

[56] References Cited

U.S. PATENT DOCUMENTS

| | | | |
|---|---|---|---|
| 3,602,825 | 8/1971 | Senior | 328/151 X |
| 3,659,211 | 4/1972 | Norton | 328/151 |
| 4,160,922 | 7/1979 | Rickenbacker | 307/353 |
| 4,166,248 | 8/1979 | Bianchi et al. | 307/246 |
| 4,215,315 | 7/1980 | Lambert et al. | 328/151 X |
| 4,225,825 | 9/1980 | Watts | 328/151 X |

Primary Examiner—John S. Heyman

[57] ABSTRACT

In circuitry in which a digital circuit samples the output of an analog circuit, the improvement of using, during an interval prior to sampling, a solid-state switching element to dissipate the charge stored in a charge storage element (e.g., capacitor) in the analog circuit.

3 Claims, 3 Drawing Figures

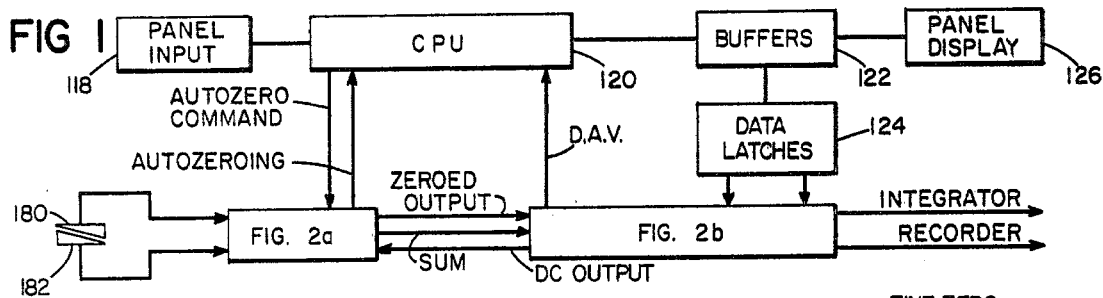
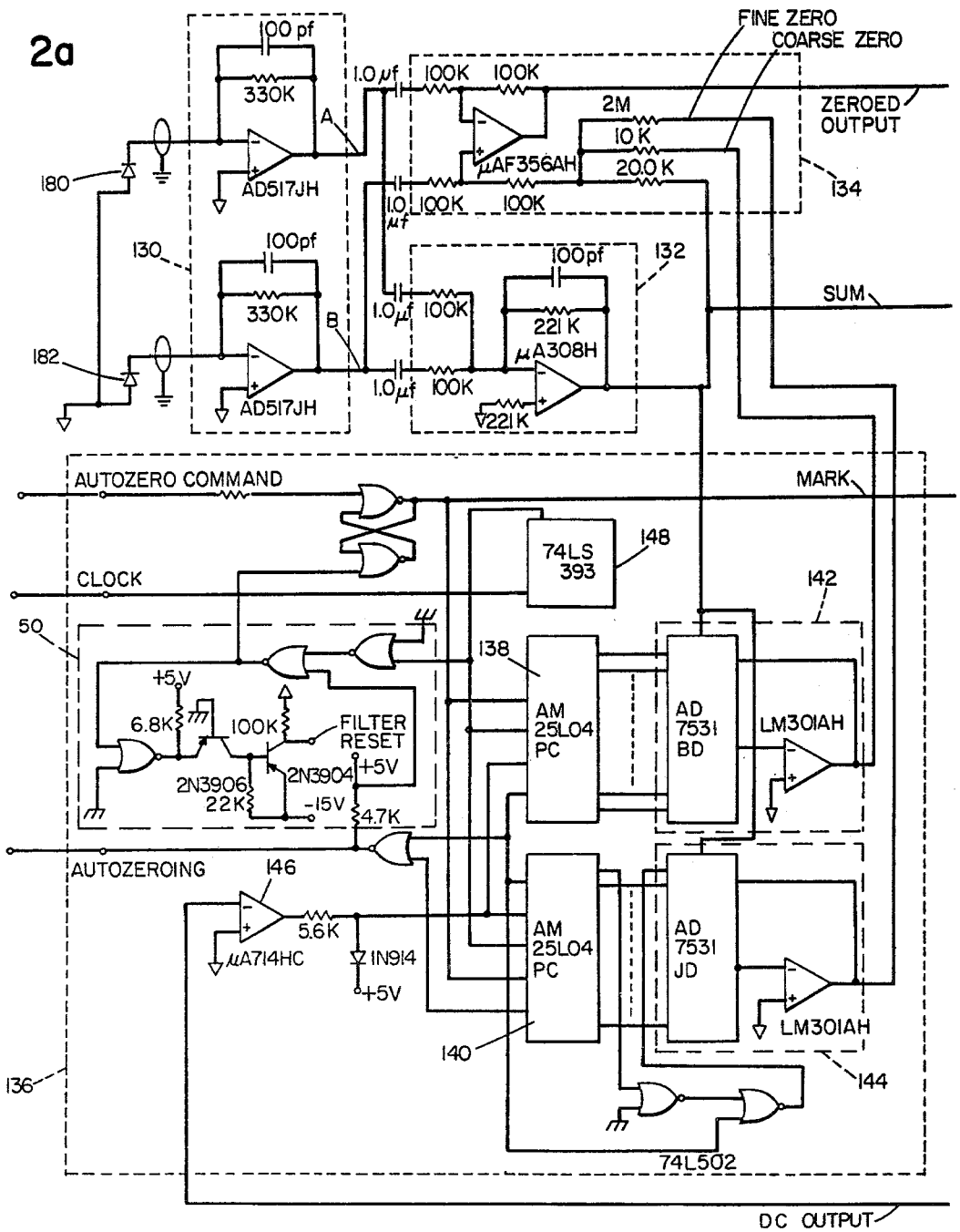

4,289,975

DISSIPATING ELECTRICAL CHARGE

FIELD OF THE INVENTION

This invention relates to circuitry for analog-to-digital and digital-to-analog conversion and similar operations.

BACKGROUND OF THE INVENTION

There are many applications (e.g., analog-to-digital and digital-to-analog conversion) in which the output of an analog circuit is repetitively sampled by a digital circuit which, in turn, changes the input to the analog circuit. Typically, a sequence of steps occur: the digital circuit chooses a digital value; the chosen digital value is applied to the analog circuit (e.g., by converting it to analog and subtracting it from an unknown analog signal); the output of the analog circuit is measured, and, based on the output, the digital circuit chooses a different digital value. The sequence of steps is repeated until the chosen digital value produces a desired result in the analog output (e.g., making the output equal to zero). Often the analog circuit will contain capacitors (or other charge-storage elements) which make the circuit slow to respond to a newly applied input. The digital circuit, on the other hand, is usually faster operating, and thus the time required to complete each sequence of steps is largely controlled by the response time of the analog circuit. For example, if the analog circuit includes a filter for smoothing out ripple and noise, it may require a few seconds for the output of the analog circuit to reach a new value. When these few seconds are multiplied by the number of times the sequence is repeated the lost waiting time can be considerable.

SUMMARY OF THE INVENTION

I have discovered that the time lost waiting for the analog circuit to respond can be shortened by dissipating (e.g., with a switch connected in parallel) the charge-storage device (e.g., capacitor) in the analog circuit. After dissipation, the analog circuit and charge-storage device are allowed to respond normally.

In preferred embodiments, the digital and analog circuits operate in a loop so that the digital circuit determines the analog input based on the analog output; the digital circuit charges the analog input so as to make the analog output approach a desired value (e.g., zero); a comparator samples the analog output; a low-pass filter in the analog circuit has one or more capacitors which form the charge storage elements; and the analog input can vary from a value far greater than the desired value to a value very close to the desired value, thereby requiring that a waiting period of many (e.g., more than five) time constants would be required before the comparator could take a sample if the capacitors were not discharged between steps.

Preferred Embodiment

The structure and operation of a preferred embodiment of the invention will now be described, after first briefly describing the drawings.

FIG. 1 is a block diagram of said embodiment.

FIGS. 2a and 2b are schematics of the electronic circuits that process the outputs of the photocells.

Figure 2B:
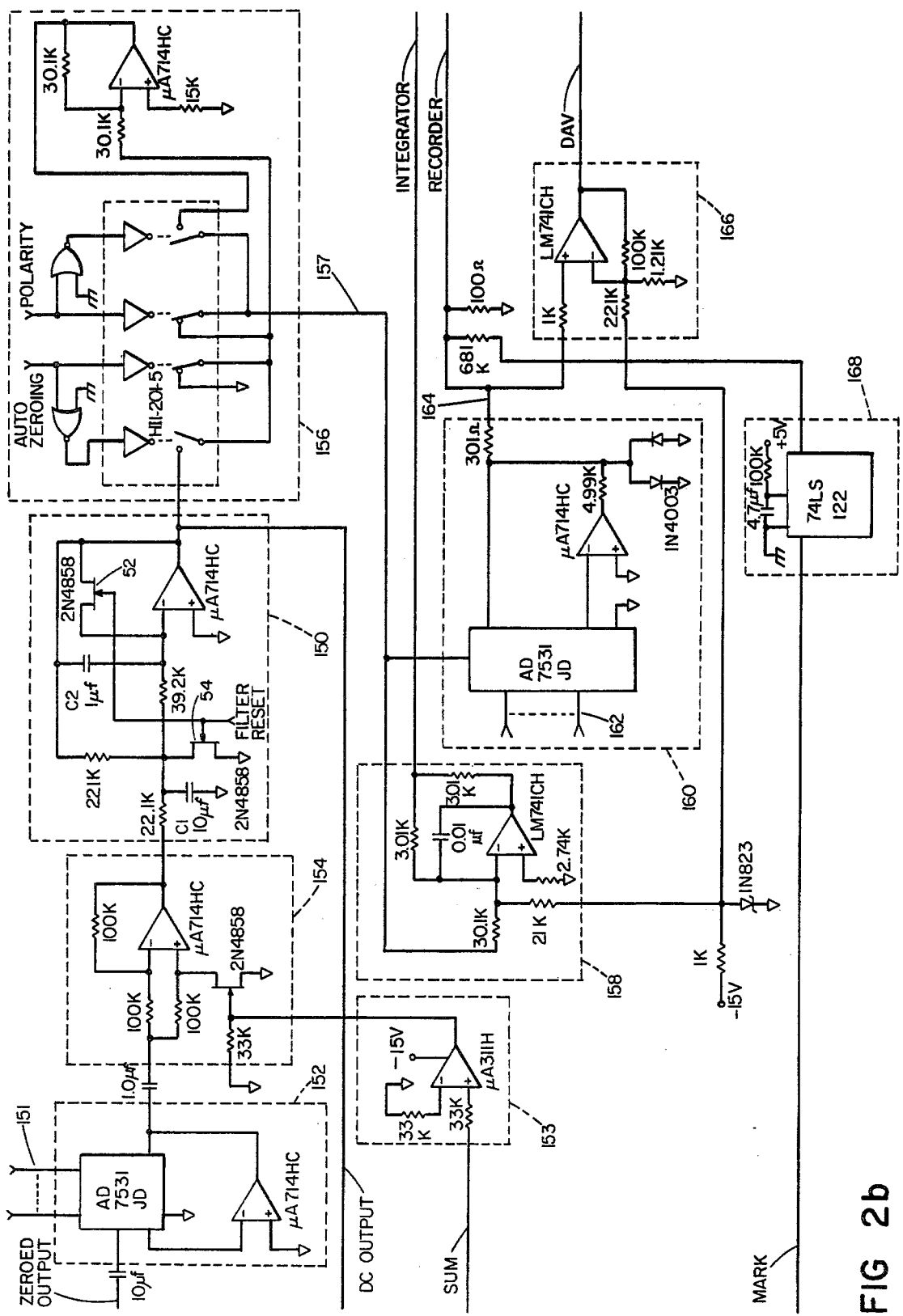

Turning to FIG. 1, there is shown a block diagram of the electronics for processing the outputs of photocells 180, 182 of a refractometer described in the copending U.S. patent application Ser. No. 51,809, of Carson et al., filed June 25, 1979 (hereby incorporated by reference). Inputs 118 from a control panel (e.g., recorder gain) are fed to a central processor 120. The central processor (CPU) initiates automatic electrical zeroing (nulling) of the photocell outputs, and sends signals via buffers 122 and gain latches 124 to circuitry shown in FIG. 2b to set the gain for display of a chromatogram on a recorder. An analog data acquisition voltage (D.A.V.) is converted to digital and sent by the processor via the input buffers to a panel display 126.

FIG. 2a shows the circuitry for electrical zeroing. The current outputs (AC signals) of photocells 180, 182 are brought via shielded cable to current-to-voltage converters 130. The AC voltages A, B produced by the converter are summed and amplified by a gain of 2.2 at amplifier 132, to form the expression $-2.2(A+B)$, which is called SUM. Amplifier 134 subtracts voltage A from voltage B, and adds to the difference the sum of three voltages: SUM, FINE ZERO, and COARSE ZERO. The latter two voltages are produced by multiplying SUM by a negative scale factor. Thus the output of amplifier 134 (ZEROED OUTPUT) can be expressed as $$[B-A] - 2.2[0.33 - 0.67 K_C - 0.0033 K_F][A+B]$$

where $K_C$ is the coarse zero scale factor and $K_F$ is the fine zero scale factor. Scale factors $K_C$, $K_F$ are set between about zero and about one by the digital circuitry of black 136, whenever a signal is sent across the AUTOZERO COMMAND lead. Normally zeroing would be done before a chromatogram was generated, but can be done at any time.

The above expression for the ZEROED OUTPUT can be presented in simplified form as $$[B-A] - K[A+B]$$

where K is the overall scale factor. The expression is independent of variations in the overall brightness of the light beam striking photocell 52 because the zeroing term $(K[A+B])$ is not a constant, but, like the difference term $(B-A)$ is proportional to beam brightness. For example, if the brightness were to rise by 10%, both the difference term and zeroing term would similarly rise by 10%, and thus the whole expression would still remain equal to zero. When beam deflection does occur, as the result of refractivity changes, the zeroing term remains roughly constant because of the complementary shape of the two cells 180, 182, which at any horizontal location have roughly the same combined vertical height.

Two successive-approximation registers 138, 140 drive a pair of digital-to-analog converters 142, 144 to form the FINE ZERO and COARSE ZERO signals. Each of converters 142, 144 multiplies the SUM signal by a scale factor set by the digital output of registers 138, 140. Registers 138, 140 follow a conventional successive approximation algorithm to select the digital outputs or scale factors. About once a second, the registers receive a clock pulse from chip 148, which produces a slow clock from the much faster processor clock signal. At each clock pulse, the output of a register is adjusted in response to the output of comparator 146 which indicates whether the applied FINE/COARSE ZERO signal is too large or too small. The input to comparator 146 which is the DC OUTPUT, produced at filter amplifier 150 (FIG. 2b). Register 138 works first to set the coarse scale factor $K_C$, and then register 140 to set the fine scale factor $K_F$. The AUTOZERO COMMAND is used by the CPU to start the autozero sequence. The AUTOZEROING signal is used to alert the central processor that the refractometer is autozeroing.

Turning to FIG. 2b, there is shown circuitry for processing the ZEROED OUTPUT. Amplifier 152 raises or lowers the signal level in response to command signals 151 from the central porcessor 120 via the data latch 124. Demodulator 154 (with the help of phase computing block 153) converts the AC signal to DC, and filter amplifier 150 smooths the DC signal. Switching block 156 operates during zeroing to turn off the RECORDER and INTEGRATOR signals. It also is used to change the polarity of the DC signal in response to a POLARITY signal from the central porcessor 120 via data latch 124. Downstream of block 156 the DC signal is processed by amplifier 158, and supplied to an integrator output lead. The DC signal is also processed by attenuator 160, under control of the central processor via signals 162. The attenuator produces a recorder output 164, which is supplied to a recorder output terminal and to amplifier 166, and a data acquisition voltage (D.A.V.), which is supplied to the central processor for panel display. Block 168 supplies a mark signal for the recorder in response to the AUTOZERO COMMAND, to indicate on the chromatogram the point at which the sample injection occurs. The CPU issues the AUTOZERO COMMAND at the time of sample injection.

A FILTER RESET connection between the zeroing circuitry and filter amplifier 150 is used during the zeroing process to discharge capacitors in the filter and reset the DC OUTPUT to approximately zero.

At each clock pulse, reset circuitry 50 supplies a signal to FETs 52, 54 in filter 150, causing them to conduct and thereby discharge capacitors C1, C2, thus setting the DC OUTPUT of the filter to approximately zero. The clock pulse is high for half of each clock interval, and thus half of each clock interval is devoted to discharging the capacitors.

Setting the DC OUTPUT to approximately zero in this manner speeds up the approximation process substantially, as it greatly reduces the time required to detect whether a selected COARSE or FINE ZERO signal is too large or too small. When the ZERO signal selected is too large, the DC OUTPUT will typically be saturated at about +14V, (or at a small positive voltage if the ZERO signal is only slightly too large). Similarly, when the ZERO signal is too small, the DC OUTPUT will typically be about −14V. Because filter 150 is designed to remove undesirable noise from the signal, it has a fairly long time constant (about 0.4 second). Thus changes in the DC OUTPUT do not occur simultaneously with a change in a ZERO signal. For example, if the ZERO signal changes such that the eventual position of the DC OUTPUT is to go from about +14V to a small negative voltage, it will take many time constants for the DC OUTPUT to reach zero volts and change polarity. Because the comparator only detects a change in polarity, long waiting times would be needed at each step just to detect whether or not a polarity change had occurred. The worst case is when the change in the DC OUTPUT is from full saturation in one polarity (e.g., +14V) to the smallest possible voltage of the opposite polarity. The smallest voltage is that voltage achieved when only the least significant bit of the FINE ZERO register is activated. Over ten time constants (about 4 seconds) would be required for the DC OUTPUT to change polarity in this worst case. Be resetting the DC OUTPUT to approximately zero at each step, this waiting period for the output to reach zero is greatly reduced, as the output starts from approximately zero volts in its slow movement toward its eventual value, and thus polarity can be detected almost immediately. Some waiting is still required (approximately one time constant) for the filter operational amplifier offset voltage and current transient effects associated with opening of the solid-state switches to decay, but it is not necessary to wait for the DC OUTPUT to settle out at its steady state value.

Other embodiments of the invention are within the following claims.

OTHER INVENTIONS

Subject matter relating to electrically zeroing the photocell using a term proportional to the photocell output was the joint invention of William W. Carson and Norman F. Rolfe and is the subject of pending U.S. patent application Ser. No. 51,809 filed June 25, 1979.

What is claimed is:

1. In circuitry of the type including analog circuit means for producing an analog output in response to an input and digital circuit means for sampling said output, said analog circuit means including a charge storage element that can become charged in response to said input, the improvement comprising charge dissipation means for dissipating the charge built up in said charge storage element during an interval prior to sampling of said output by said digital circuit means, wherein said digital circuit means and analog circuit means are connected in a loop and said digital means includes means for providing said input to said analog circuit and for periodically changing said input in response to changes in said sampled output, wherein said digital circuit means includes means for changing said input so that said output approaches a desired value, wherein said digital circuit means includes comparator means for measuring whether said output is above or below said desired value and includes means for adjusting said input to said analog circuit based on the output of said comparator, wherein said analog circuit means includes a low-pass filter which includes one or more capacitors which form said charge storage element, the response of said filter being characterized by a time constant, and wherein said digital circuit means includes means for varying said input so that at two successive sampling times said analog output can change from a first value greater than said desired value to a second value less than said desired value, the amount by which said second value is less than said desired value being 100 or more times smaller than the amount by which said first value exceeds said desired value, whereby the time required, without dissipation of the charge stored in said capacitors, for said output to change from being above to being below said desired value, and thereby allow said comparator output to change, is of the order of 5 or more said time constants.

2. The circuitry of claim 1 wherein said time constant is greater than 0.05 seconds.

3. The circuitry of claim 1 wherein said desired value is zero, said first value is a positive or negative full-scale voltage, and said second value is a voltage of opposite polarity to said first value and reduced in magnitude by greater than a factor of 100.

* * * * *